United States Patent

Ansmann et al.

[11] Patent Number: 6,147,124
[45] Date of Patent: Nov. 14, 2000

[54] POURABLE NACREOUS LUSTRE CONCENTRATE

[75] Inventors: Achim Ansmann, Erkrath; Rolf Kawa, Monheim; Helga Gondek, Duesseldorf, all of Germany

[73] Assignee: Henkel Kommanditgesellschaft auf Aktien, Germany

[21] Appl. No.: 08/983,628

[22] PCT Filed: Jul. 16, 1996

[86] PCT No.: PCT/EP96/03117

§ 371 Date: Apr. 16, 1998

§ 102(e) Date: Apr. 16, 1998

[87] PCT Pub. No.: WO97/05224

PCT Pub. Date: Feb. 13, 1997

[30] Foreign Application Priority Data

Jul. 25, 1995 [DE] Germany .......... 195 27 120

[51] Int. Cl.[7] .......... B01F 3/08; B01F 3/12; B01F 17/00; C11D 1/825

[52] U.S. Cl. .......... 516/69; 516/77; 516/900; 510/416; 510/126; 510/159; 510/502; 424/70.19; 424/70.31

[58] Field of Search .......... 516/69, 77, 203, 516/900; 424/70.19, 70.31; 510/126, 137, 130, 138, 159, 416, 502

[56] References Cited

U.S. PATENT DOCUMENTS

| 5,500,155 | 3/1996 | Weuthen et al. | 510/502 |
|---|---|---|---|
| 5,545,354 | 8/1996 | Ofosu-Asante | 510/502 |
| 5,711,899 | 1/1998 | Kawa et al. | 510/416 |
| 5,789,372 | 8/1998 | Fabry | 510/502 |

FOREIGN PATENT DOCUMENTS

| 2 006 248 | 6/1990 | Canada. |
| 2 103 578 | 8/1992 | Canada. |
| 0 221 465 | 5/1987 | European Pat. Off.. |
| 0 300 379 | 1/1989 | European Pat. Off.. |
| 0 332 805 | 9/1989 | European Pat. Off.. |
| 0 376 083 | 7/1990 | European Pat. Off.. |
| 41 03 551 | 8/1992 | Germany. |
| 44 00 632 | 3/1995 | Germany. |
| 195 11 569 | 10/1996 | Germany. |
| WO95/03782 | 2/1995 | WIPO. |

OTHER PUBLICATIONS

Bailey's Industrial Oil and Fat Products 1:646–49 (4th ed. 1979) month unavilable.

*Primary Examiner*—Richard D. Lovering
*Assistant Examiner*—Daniel S. Metzmaier
*Attorney, Agent, or Firm*—John E. Drach; Glenn E. J. Murphy

[57] ABSTRACT

A free-flowing pearlescer concentrate is presented which is composed of: (a) 5 to 50% by weight of a pearlescing component which is (1) a compound of formula $R^3$—$(OC_nH_{2n})_x$—$OR^4$ where $R^3$ is a fatty acyl group having 14 to 22 carbon atoms, $R^4$ is hydrogen or linear fatty acyl group having 14 to 22 carbon atoms, n is 2 or 3, and x is 1; (2) a compound of formula $R_5$—CO—NH—X, where $R^5$ is an alkyl group having 8 to 22 carbon atoms and X is selected from the group —$CH_2$—$CH_2$—OH, —$CH_2$—$CH_2$—$CH_2$—OH, and —$C(CH_3)_2$—OH; and a linear saturated fatty acid having 12 to 14 carbon atoms; (b) 5 to 55% by weight of a fatty acid-N-alkyl polyhydroxyalkylamide nonionic emulsifier of the formula $$R^1\text{---}CO\text{---}N(R^2)\text{---}R^z$$

as the sole emulsifier, where $R^1$—CO is an aliphatic acyl group having 6 to 22 carbon atoms, $R^2$ is an alkyl or hydroxyalkyl group having 1 to 4 carbon atoms, and $R^z$ is a linear or branched polyhydroxyalkyl radical having 3 to 12 carbon atoms and 3 to 10 hydroxyl groups, and (c) 0.1% to 40% by weight of a low molecular weight polyhydric alcohol. The concentrate exhibits brilliant pearlescence and is biodegradable.

3 Claims, No Drawings

POURABLE NACREOUS LUSTRE CONCENTRATE

This application is a U.S. national stage application filed under 35 U.S.C. 371, claiming benefit under 35 U.S.C. §120 of PCT/EP96/03117, filed Jul. 16, 1996.

BACKGROUND OF THE INVENTION

1. Field of the Invention

This invention relates to a pearlescer concentrate in the form of a free-flowing or pumpable aqueous dispersion containing 5 to 50% by weight of pearlescing components.

2. Discussion of the Related Art

Aqueous formulations of surfactants and cosmetic preparations can be given an aesthetically attractive pearlescent appearance by incorporation of substances which, after cooling, precipitate in the form of fine pearlescent crystals and remain dispersed in the formulations. Suitable pearlescers are, for example, the monoesters, diesters and optionally triesters of ethylene glycol, propylene glycol and oligomeric alkylene glycols of this type or glycerol with $C_{14-22}$ fatty acids, fatty acids and monoalkanolamides of fatty acids.

It is also known that the pearlescers mentioned above can be stably dispersed in water or in aqueous surfactant solutions and that the concentrated pearlescer dispersions obtained in this way can be added without heating to the formulations to be given a pearlescent appearance so that there is no need for the heating and cooling otherwise necessary for incorporation to form the pearlescent crystals.

Although a relatively wide range of largely satisfactory pearlescer concentrates is available today, attempts are still being made to develop concentrates which are distinguished by particularly brilliant pearlescence.

Attempts are also being made to develop pearlescer concentrates with excellent properties where the emulsifier base is made up completely or predominantly of nonionic surfactants. Pearlescer concentrates such as these may generally be used without any regard for the types of emulsifier in the end product. Efforts are also being made to formulate pearlescer concentrates with a surfactant base which is distinguished by ready biodegradability.

It has now been found that pearlescer concentrates based on fatty acid-N-alkyl polyhydroxyalkylamide emulsifiers satisfy these requirements particularly well.

SUMMARY OF THE INVENTION

Accordingly, the present invention relates to pearlescer concentrates in the form of a free-flowing aqueous dispersion containing 5 to 50% by weight of pearlescing components and 5 to 55% by weight of emulsifiers, characterized in that they contain fatty acid-N-alkyl polyhydroxyalkylamides corresponding to general formula (I):

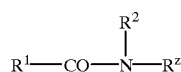

(I)

in which $R^1$—CO is an aliphatic acyl group containing 6 to 22 carbon atoms, $R^2$ is hydrogen, an alkyl or hydroxyalkyl group containing 1 to 4 carbon atoms and $R^z$ is a linear or branched polyhydroxyalkyl radical containing 3 to 12 carbon atoms and 3 to 10 hydroxyl groups, as emulsifiers.

DESCRIPTION OF THE INVENTION

In the context of the invention, pearlescing components are understood to be meltable fats or waxes which, on cooling of aqueous solutions or emulsions thereof, crystallize out at temperatures of about 30 to 90° C. in the form of fine pearlescent crystals.

These meltable fats or waxes include
esters corresponding to formula (II):

$$R^3-(OC_nH_{2n})_x-OR^4 \quad (II)$$

in which $R^3$ is a linear fatty acyl group containing 14 to 22 carbon atoms, $R^4$ is hydrogen or has the same meaning as $R^3$, n is the number 2 or 3 and x is a number of 1 to 4, monoalkanolamides corresponding to general formula (III):

$$R^5-CO-NH-X \quad (III)$$

in which $R^5$ is an alkyl group containing 8 to 22 carbon atoms and, more particularly, 8 to 18 carbon atoms and X is a —$CH_2$—$CH_2$—OH group, a —$CH_2$—$CH_2$—$CH_2$—OH group or a —$C(CH_3)_2$—OH group, linear saturated fatty acids containing 14 to 22 carbon atoms and monoesters, diesters and triesters of glycerol with linear saturated fatty acids containing 14 to 22 carbon atoms.

Examples of esters corresponding to the general formula $R^3(OC_nH_{2n})_xOR^4$ are the monoesters and diesters of ethylene glycol and propylene glycol with higher fatty acids, for example with palmitic acid, stearic acid or behenic acid, or the diesters of diethylene glycol or triethylene glycol with such fatty acids. Also suitable are mixtures of monoesters and diesters of the glycols mentioned with fatty acid mixtures, for example with hydrogenated tallow fatty acid, palm oil fatty acid or with the saturated $C_{14-18}$ fatty acid fraction of tallow fatty acid. The ethylene glycol monoesters and/or diesters of palmitic and/or stearic acid are particularly suitable.

Preferred monoalkanolamides are the monoethanolamides. The compounds may contain alkyl groups of a single type. However, the alkanolamides may also be produced from fatty acid mixtures from natural sources, for example cocofatty acids, so that corresponding mixtures of alkyl groups are present.

The linear fatty acids may be, for example, palmitic acid, stearic acid, arachic acid or behenic acid, although technical fatty acid cuts consisting entirely or predominantly of $C_{16-22}$ fatty acids, for example palmitic/stearic acid fractions obtained from tallow fatty acid or palm oil fatty acid by separation of the fatty acids liquid at +5° C. or palmitic/stearic acid fractions obtainable by hydrogenation of tallow fatty acid or palm oil fatty acid, are also suitable.

The glycerol esters suitable for use in the teaching according to the invention include the monoesters, diesters and in particular triesters with lauric acid, myristic acid, palmitic acid, stearic acid and behenic acid and with mixtures of these fatty acids.

The pearlescer concentrates according to the invention may contain both exclusively representatives of one of these classes of compounds and mixtures of representatives of several of these classes of compounds.

Preferred pearlescing components are representatives of the first three classes mentioned.

However, fatty acid monoalkanolamides or dialkanolamides and derivatives thereof have recently been suspected of involvement in the formation of nitrosamines. Accordingly, it may be desirable to formulate cosmetic preparations without these alkanolamides and alkanolamide derivatives. For this reason, compounds belonging to classes 1 and 3 may be particularly preferred pearlescing components.

Pearlescer concentrates in which at least 70% by weight and, more particularly, at least 90% by weight of the pearlescing components consist of ethylene glycol distearate are most particularly preferred.

Another particularly preferred embodiment is characterized by the use of mixtures of the ethylene glycol fatty acid esters which are disclosed in German patent application 195 11 569.4.

The pearlescer concentrates contain emulsifiers of the fatty acid-N-alkyl polyhydroxyalkylamide type as another essential component. These compounds correspond to the following general formula (I):

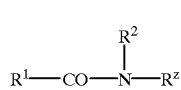

(I)

in which $R^1$—CO is an aliphatic acyl group containing 6 to 22 carbon atoms, $R^2$ is hydrogen, an alkyl or hydroxyalkyl group containing 1 to 4 carbon atoms and $R^z$ is a linear or branched polyhydroxyalkyl group containing 3 to 12 carbon atoms and 3 to 10 hydroxyl groups.

These compounds are known from the literature and may normally be obtained by reductive amination of a reducing sugar with ammonia, an alkylamine or an alkanolamine and subsequent acylation with a fatty acid, a fatty acid alkyl ester or a fatty acid chloride.

The fatty acid-N-alkyl polyhydroxyalkylamides are preferably derived from reducing sugars containing 5 to 6 carbon atoms, more particularly from glucose. According to the invention, therefore, fatty acid-N-alkyl glucamides corresponding to formula (IV):

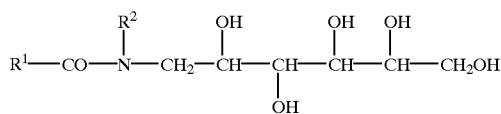

(IV)

are preferred fatty acid-N-alkyl polyhydroxyalkylamides. Fatty acid-N-alkyl polyhydroxyalkylamides corresponding to formula (I) and fatty acid-N-alkyl glucamides corresponding to formula (IV), where $R^2$ is water or an alkyl group, are also preferred as are compounds in which $R^1$—CO is the acyl group of caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, arachic acid, gadoleic acid, behenic acid or erucic acid or the mixtures thereof obtained, in particular, in the working up of natural oils and fats on an industrial scale. Acyl groups $R^1$—CO containing 12 to 18 carbon atoms are particularly preferred.

Fatty acid-N-alkyl glucamides corresponding to formula (IV) obtained by the reductive amination of glucose with methylamine and subsequent acylation with lauric acid or $C_{12/14}$ cocofatty acid or a corresponding derivative are most particularly preferred. Compounds in which the polyhydroxyalkyl group is derived from maltose or palatinose have also proved to be suitable for the purposes of the invention.

Further information on the production and properties of these compounds can be found in the literature. Reference is expressly made to the relevant disclosure of German patent 44 00 632 C1.

The pearlescer concentrates according to the invention contain the emulsifiers of the fatty acid-N-alkyl polyhydroxyalkylamide type corresponding to formula (I) in quantities of preferably 5 to 30% by weight and, more preferably, 5 to 15% by weight, based on the concentrate as a whole.

The pearlescer concentrates according to the invention may contain the fatty acid-N-alkyl polyhydroxyalkylamides mentioned as sole emulsifiers. This is a preferred embodiment of the invention.

However, in another preferred embodiment, other emulsifiers may also be present, depending on the particular application envisaged for the pearlescer concentrates. In principle, these emulsifiers may be both nonionic emulsifiers and ionic emulsifiers. Suitable ionic emulsifiers are both cationic and, in particular, anionic, zwitterionic and ampholytic emulsifiers.

Anionic emulsifiers suitable for use in accordance with the invention are, for example, alkyl sulfates and alkyl polyethylene glycol ether sulfates containing 8 to 22 carbon atoms in the alkyl chain and 1 to 15 and, more particularly, 1 to 6 ethylene glycol ether groups in the molecule which are used in the form of their alkali metal, magnesium, ammonium, mono-, di- or trialkanolammonium salts containing 2 to 3 carbon atoms in the alkanol group. Other suitable anionic surfactants are alkane sulfonates, α-olefin sulfonates, α-sulfofatty acid methyl esters, fatty alcohol (polyglycol ether) carboxylates, sulfosuccinic acid mono- and dialkyl esters, sulfosuccinic acid ester salts, acyl isethionates, acyl taurides and acyl sarcosides containing 8 to 22 and, more particularly, 12 to 18 carbon atoms in the alkyl or acyl chain. Soaps may also be used as emulsifiers. This may be done, for example, by saponifying a small amount, i.e. about 1 to 20% by weight, of the linear saturated fatty acids with added alkali metal hydroxide and thus converting it into an anionic emulsifier.

Preferred anionic emulsifiers are alkyl polyethylene glycol ether sulfates such as, for example, sodium lauryl polyglycol ether sulfate.

Zwitterionic surfactants may also be used as emulsifiers. Zwitterionic surfactants are surface-active compounds which contain at least one quaternary ammonium group and at least one —COO$^{(-)}$ or —SO$_3^{(-)}$ group in the molecule. Particularly suitable zwitterionic surfactants are the so-called betaines, such as N-alkyl-N,N-dimethylammonium glycinates, for example cocoalkyl dimethylammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group, and cocoacylaminoethyl hydroxyethyl carboxymethyl glycinate. A preferred zwitterionic surfactant is the fatty acid amide derivative known under the INCI name of Cocamidopropyl Betaine.

Other suitable emulsifiers are ampholytic surfactants. Ampholytic surfactants are surface-active compounds which, in addition to a $C_{8-18}$ alkyl or acyl group, contain at least one free amino group and at least one —COOH or —SO$_3$H group in the molecule and which are capable of forming inner salts. Examples of suitable ampholytic surfactants are N-alkyl glycines, N-alkyl propionic acids, N-alkyl aminobutyric acids, N-alkyl iminodipropionic acids, N-hydroxyethyl-N-alkylamidopropyl glycines, N-alkyl taurines, N-alkyl sarcosines, 2-alkylaminopropionic acids and alkylaminoacetic acids containing about 8 to 18 carbon atoms in the alkyl group. Particularly preferred ampholytic surfactants are N-cocoalkylaminopropionate, cocoacylaminoethyl aminopropionate and $C_{12-18}$ acyl sarcosine.

Quaternary ammonium surfactants, for example alkyl trimethyl ammonium chlorides and dialkyl dimethyl ammonium chlorides, for example cetyl trimethyl ammonium chloride, stearyl trimethyl ammonium chloride, distearyl dimethyl ammonium chloride, lauryl dimethyl ammonium chloride and lauryl dimethylbenzyl ammonium chloride, cetyl pyridinium chloride and tallow alkyl-tris-(oligooxyalkyl)-ammonium phosphate are mentioned as cationic emulsifiers. Readily biodegradable quaternary ester compounds, for example the dialkyl ammonium methosulfates and methyl hydroxyalkyl dialkoyloxyalkyl ammonium methosulfates marketed under the registered name of Stepantex®, may also be used as cationic surfactants.

Finally, nonionic emulsifiers which contain, for example, a polyol group, a polyalkylene glycol ether group or a combination of polyol and polyglycol ether groups as the hydrophilic group may also be used.
Examples of such compounds are:
- addition products of 2 to 30 moles of ethylene oxide and/or 0 to 5 moles of propylene oxide with linear $C_{8-22}$ fatty alcohols, with $C_{12-22}$ fatty acids and with alkylphenols containing 8 to 15 carbon atoms in the alkyl group,
- $C_{12-22}$ fatty acid monoesters and diesters of adducts of 1 to 30 moles of ethylene oxide with glycerol,
- glycerol monoesters and diesters and sorbitan monoesters and diesters of saturated and unsaturated $C_{8-22}$ fatty acids and ethylene oxide adducts thereof and
- addition products of 5 to 60 moles of ethylene oxide with castor oil and hydrogenated castor oil.

Particularly preferred nonionic emulsifiers are alkyl polyglycosides corresponding to general formula (IV):

$$R^6O\text{—}(Z)_y \qquad (IV)$$

in which $R^6$ is an alkyl group containing 6 to 22 carbon atoms, Z is a mono- or oligosaccharide, y is a number of 1.1 to 5,
or addition products thereof with 1 to 10 molecules of ethylene oxide and/or propylene oxide.

The alkyl polyglycosides corresponding to formula (IV) are further characterized by the following parameters:

The alkyl group $R^6$ contains 6 to 22 carbon atoms and may be both linear and branched. Primary, linear and 2-methyl-branched aliphatic groups are preferred. Examples of such alkyl groups are 1-octyl, 1-decyl, 1-lauryl, 1-myristyl, 1-cetyl and 1-stearyl. 1-Octyl, 1-decyl, 1-lauryl and 1-myristyl are particularly preferred. Where so-called "oxoalcohols" are used as starting materials, compounds containing an odd number of carbon atoms in the alkyl chain predominate.

The alkyl glycosides suitable for use in accordance with the invention may contain alkyl groups $R^6$ of only one partiular type. However, these compounds are normally produced from natural fats and oils or mineral oils. In this case, mixtures corresponding to the starting compounds or to the particular way in which these compounds are worked up are present as the alkyl groups R.

Particularly preferred alkyl polyglycosides are those in which $R^6$ consists
- essentially of $C_8$ and $C_{10}$ alkyl groups,
- essentially of $C_{12}$ and $C_{14}$ alkyl groups,
- essentially of $C_8$ to $C_{16}$ alkyl groups,
- essentially of $C_{12}$ to $C_{16}$ alkyl groups, Any mono- or oligosaccharides may be used as the sugar unit Z. Sugars containing 5 or 6 carbon atoms and the corresponding oligosaccharides are normally used. Examples of such sugars are glucose, fructose, galactose, arabinose, ribose, xylose, lyxose, allose, altrose, mannose, gulose, idose, talose and sucrose. Preferred sugar units are glucose, fructose, galactose, arabinose and sucrose, glucose being particularly preferred.

The alkyl polyglycosides suitable for use in accordance with the invention contain on average 1.1 to 5 sugar units. Alkyl glycosides where y is a number of 1.1 to 2 are preferred, alkyl glycosides where y is a number of 1.1 to 1.4 being most particularly preferred.

Alkoxylated homologs of the alkyl polyglycosides mentioned may also be used in accordance with the invention. These homologs may contain on average up to 10 ethylene oxide and/or propylene oxide units per alkyl glycoside unit. These products, too, are not normally uniform compounds, but have a homolog distribution corresponding to the particular ethoxylation process selected. Alkoxylated compounds such as these may be obtained, for example, by using ethoxylated fatty alcohols for the synthesis of the alkyl polyglycosides. However, it is preferred to use the non-alkoxylated compounds for the purposes of the teaching according to the invention.

The compounds containing alkyl groups used as surfactants may be individual compounds. However, it is generally preferred to produce the substances in question from native vegetable and animal raw materials so that mixtures differing in their alkyl chain lengths according to the particular raw material used are obtained.

The surfactants which represent addition products of ethylene and/or propylene oxide with fatty alcohols may be both products with a "normal" homolog distribution and products with a narrow homolog distribution. Products with a "normal" homolog distribution are understood to be mixtures of homologs which are obtained in the reaction of fatty alcohol and alkylene oxide using alkali metals, alkali metal hydroxides or alkali metal alcoholates as catalysts. By contrast, narrow homolog distributions are obtained when, for example, hydrotalcites, alkaline earth metal salts of ether carboxylic acids, alkaline earth metal oxides, hydroxides or alcoholates are used as catalysts. The use of so-called narrow-range products can be advantageous.

According to the invention, the pearlescer concentrates may contain representatives of one or more of the surfactant classes mentioned.

Since pearlescer concentrates are mainly added to formulations containing anionic surfactants, the pearlescer concentrates according to the invention—in one preferred embodiment—contain only anionic emulsifiers as further emulsifiers.

In addition, the pearlescer concentrates according to the invention which contain nonionic, zwitterionic and/or ampholytic surfactants have proved to be particularly universal in their usefulness and to be particularly compatible with aqueous formulations of water-soluble surfactants of any type and ionicity. In another preferred embodiment, the pearlescer concentrates according to the invention contain emulsifiers of these types only, more particularly nonionic emulsifiers only, as further emulsifiers.

In another preferred embodiment, the pearlescer concentrates according to the invention may additionally contain low molecular weight polyhydric alcohols. The pumping behavior and flow behavior of the pearlescer concentrates and their handling behavior in particular can be improved by the presence of such alcohols.

Low molecular weight polyhydric alcohols of a preferred group contain 2 to 12 carbon atoms and 2 to 10 hydroxyl groups. Examples of such alcohols include ethylene glycol, 1,2- and 1,3-propylene glycol, glycerol, erythritol, arabitol, adonitol, xylitol, sorbitol, mannitol, dulcitol, glucose and sucrose. It is particularly preferred to use glycerol, 1,2-propylene glycol, 1,3-propylene glycol, sorbitol and/or glucose.

The use of glycerol as a low molecular weight polyhydric alcohol leads to pearlescer concentrates which provide the end products with particularly brilliant pearlescence.

Another group of preferred low molecular weight polyhydric alcohols is formed by oligomeric ethers, more particularly based on ethylene glycol, propylene glycol and glycerol. Products with an average molecular weight below about 700 dalton are particularly suitable. Above all, the oligomers of ethylene glycol and glycerol, more particularly the dimers, trimers and tetramers, may be used in accordance with the invention.

According to the invention, the low molecular weight polyhydric alcohols are used in quantities of preferably 0.1 to 40% by weight, based on the formulation as a whole. Quantities of 0.1 to 10% by weight of low molecular weight polyhydric alcohols have a particularly positive effect on pumping behavior and flow behavior while quantities of more than 10% by weight, based on the pearlescer concentrate as a whole, can often replace a special preservative.

Besides the constituents mentioned above, the pearlescer concentrates according to the invention essentially contain water.

In addition, small quantities of buffering substances, for example citric acid and/or sodium citrate, may be present to adjust the pH to a value of 2 to 8 while inorganic salts, for example sodium chloride, may be present as thickeners.

In a first preferred embodiment, the pearlescer concentrates according to the invention contain typical preservatives known to the expert. Examples of such preservatives are formic acid, benzoic acid and pHB esters.

In a second preferred embodiment, the pearlescer concentrates are preservative-free. Preservative-free pearlescer concentrates are understood to be pearlescer concentrates to which no preservatives have been added. Accordingly, the pearlescer concentrates preferably contain no preservatives or only those quantities of preservatives which are introduced through the individual raw materials selected.

The pearlescer concentrates according to the invention may be produced by first heating components (A), (B) and (C) together to a temperature about 1 to 30° C. above the melting point. In most cases, this will be a temperature of about 60 to 90° C. The water heated to substantially the same temperature is then added to the resulting mixture. If an ionic water-soluble emulsifier is used as the emulsifier, it may be preferable to dissolve the emulsifier in the water phase and to introduce it into the mixture together with the water. The aqueous phase may already contain the buffers in dissolved form. The dispersion formed is then cooled with stirring to room temperature, i.e. to around 25° C. In most cases, the viscosity of the pearlescer concentrate is so low that there is no need to use special stirring units, such as homogenizers or other high-speed mixers.

The pearlescer concentrates according to the invention are suitable for the production of clouded and pearlescent liquid, aqueous formulations of water-soluble surfactants. They may be incorporated, for example, in liquid detergents and cleaners, such as dishwashing detergents, liquid light-duty detergents and liquid soaps, but are preferably incorporated in liquid bodycleansing and body-care formulations such as, for example, shampoos, liquid hand-washing formulations and body shampoos, shower bath preparations, bath additives (foam baths), hair rinses or hair colorants.

To produce pearlescence, the pearlescer concentrates according to the invention are added to the clear aqueous formulations at 0 to 40° C. in a quantity of 0.5 to 20% by weight and, more particularly, in a quantity of 1.5 to 10% by weight of the formulation and dispersed therein by stirring. A brightly sparkling, dense to gently sparkling, extremely dense pearlescence is formed according to the particular formulation and the concentration used.

The following Examples are intended to illustrate the invention.

EXAMPLES

| Pearlescer concentrates (all figures are parts by weight) | | | | |
|---|---|---|---|---|
| | 1 | 2 | 3 | 4 |
| $C_{12}$-N-methyl glucamide | 11 | 5 | 8 | 5 |
| Plantaren 1200[1] | — | 20 | — | — |
| Dehydol LS 4[2] | — | — | 10 | 5 |
| Texapon N 70[3] | — | — | — | 20 |
| Cutina AGS[4] | 20 | 15 | 25 | 30 |
| Glycerol | 16 | — | — | 2 |
| Polydiol 400[5] | — | — | 20 | — |
| Water, viscosity and pH regulators | to 100 | to 100 | to 100 | to 100 |

[1]$C_{12-16}$ fatty alcohol-1,4-glucoside (ca. 50% active substance in water; INCI name: Lauryl Polyglycose) (HENKEL)
[2]$C_{12-14}$ fatty alcohol + 4 ethylene oxide (HENKEL)
[3]Sodium lauryl ether sulfate (ca. 72% active substance in water; INCI name: Sodium Laureth Sulfate) (HENKEL)
[4]Ethylene glycol distearate (at least 90% diester; INCI name: Glycol Distearate) (HENKEL)
[5]Polyethylene glycol (HENKEL CORP.)

What is claimed is:

1. A pearlescer concentrate in the form of a free flowing aqueous dispersion consisting essentially of:
   (a) 5 to 50% by weight of a pearlescing component selected from the group consisting of
      (1) a compound of formula (II):

$$R^3\text{—}(OC_nH_{2n})_x\text{—}OR^4 \qquad (II)$$

or mixtures thereof, wherein $R^3$ is a fatty acyl group having 14 to 22 carbon atoms, $R^4$ is hydrogen or linear fatty acyl group having 14 to 22 carbon atoms, n is 2 or 3, and x is 1;
      (2) a compound of formula (III):

$$R^5\text{—}CO\text{—}NH\text{—}X \qquad (III)$$

or a mixture thereof, wherein $R^5$ is an alkyl group having 8 to 22 carbon atoms and X is selected from the group consisting of —$CH_2$—$CH_2$—OH, —$CH_2$—$CH_2$—$CH_2$—OH, and —$C(CH_3)_2$—OH; and
      (3) a linear saturated fatty acid having 12 to 14 carbon atoms;
   (b) 5 to 55% by weight of a nonionic emulsifier of formula (I):

$$R^1\text{—}CO\text{—}\underset{\underset{R^2}{|}}{N}\text{—}R^z \qquad (I)$$

or a mixture thereof as the sole emulsifier, in which formula (I) $R^1$—CO is an aliphatic acyl group having 6 to 22 carbon atoms, $R^2$ is an alkyl or hydroxyalkyl group having 1 to 4 carbon atoms, and $R^z$ is a linear or branched polyhydroxyalkyl radical having 3 to 12 carbon atoms and 3 to 10 hydroxyl groups; and
   (c) 0.1% to 40% by weight of a low molecular weight polyhydric alcohol.

2. A pearlescer concentrate according to claim 1 wherein $R^5$ is an alkyl group having 8 to 18 carbon atoms.

3. A pearlescer concentrate according to claim 1, wherein the low molecular weight polyhydric alcohol is selected from the group consisting of glycerol, 1,2-propylene glycol, 1,3-propylene glycol, glucose and sorbitol.

* * * * *